United States Patent
Moore

(10) Patent No.: US 10,625,177 B2
(45) Date of Patent: Apr. 21, 2020

(54) BIOAVAILABLE CANNABIS PLANT BLEND

(71) Applicant: David Harold Moore, Henderson, NV (US)

(72) Inventor: David Harold Moore, Henderson, NV (US)

(73) Assignee: David Harold Moore

( * ) Notice: Subject to any disclaimer, the term of this patent is extended or adjusted under 35 U.S.C. 154(b) by 365 days.

(21) Appl. No.: 15/699,377

(22) Filed: Sep. 8, 2017

(65) Prior Publication Data

US 2019/0076756 A1    Mar. 14, 2019

(51) Int. Cl.
| | |
|---|---|
| *A61K 36/00* | (2006.01) |
| *B01D 17/00* | (2006.01) |
| *C07D 311/80* | (2006.01) |
| *A61K 36/185* | (2006.01) |
| *A61K 31/352* | (2006.01) |
| *A61K 36/73* | (2006.01) |

(52) U.S. Cl.
CPC ............ *B01D 17/00* (2013.01); *A61K 36/185* (2013.01); *C07D 311/80* (2013.01); *A61K 31/352* (2013.01); *A61K 36/73* (2013.01)

(58) Field of Classification Search
CPC ..................................................... A61K 36/00

USPC ......................................................... 424/725
See application file for complete search history.

(56) References Cited

FOREIGN PATENT DOCUMENTS

CN          102422904 A    *   4/2012

* cited by examiner

*Primary Examiner* — Michael V Meller

(57) ABSTRACT

The present invention provides a step-by-step process for transforming the raw cannabis plant into an infused and bioavailable cannabis-plant-blend that can be used as a stand-alone food supplement; and can be integrated into tobacco replacement products, edible food products, or infused beverages of any kind. This unique and novel process includes multiple decarboxylation steps and produces a bioavailable cannabis product, which is inclusive of an infused amalgam of either: both heat-cooked and raw cannabis, or just heat-cooked cannabis; along with an infused blend of various chemical compounds. This process reduces the amount of waste product because it includes much of the utilized cannabis plant-matter in the final amalgam; while utilizing a twice, thrice, or four times heat-cooked cannabis product which is also blended and infused with various chemical compounds; so as to produce the final amalgam, which includes a portion or all of the utilized cannabis plant-matter, and which has been named the bioavailable cannabis plant blend.

1 Claim, 1 Drawing Sheet

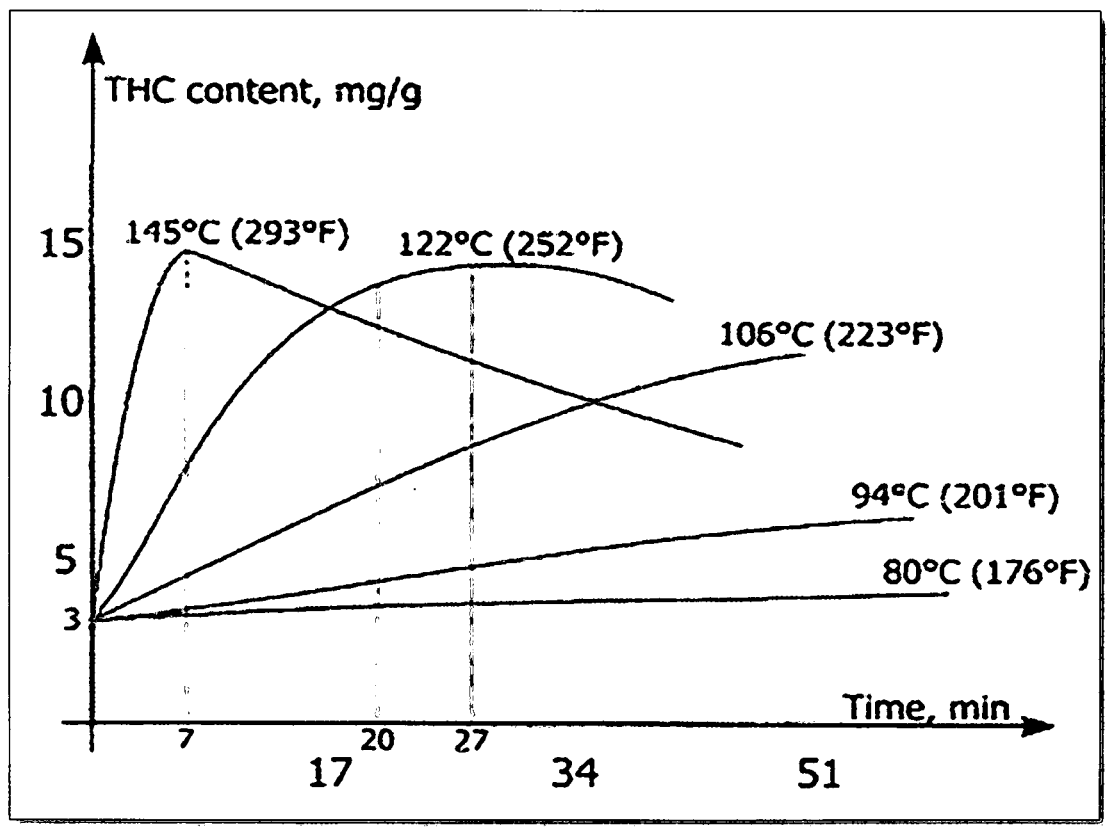

BIOAVAILABLE CANNABIS PLANT BLEND

BACKGROUND

I have suffered from a High Functioning form of Autism, known as Asperger's Syndrome, since I was born. The autism caused the dysregulation of my endocannabinoid immune system, which caused the autoimmune disorder known as Celiac Disease, which then turned into cancer of the stomach lining. And only after going into renal failure, did I begin to look for a solution.

Then I read a recent study from the Biomedical Center for Autism Research and Treatment, which suggests the CB2 receptor as a potential therapeutic target for the cannabis. This study was the first to demonstrate the up-regulation of CB2 receptors in autistic endocannabinoid systems.

The CB2 receptor enhancements demonstrate that the endocannabinoid system is involved in the maintenance of autism. According to the findings, the endocannabinoid system may represent a novel treatment opportunity for cannabis therapy with autistic minds. And that's because the up-regulation of the CB2 receptors enhances the peripheral organs ability to manage the immune system. And endocannabinoid signaling, in general, affects learning, pain, and other important regenerative processes.

You see, the endocannabinoid system is an intricate network of endocannabinoids, their receptors, and the associated enzymes; and all play critical roles in maintaining the body's homeostasis. And our biochemical homeostasis is unique to each one of us. It is therefore important to note, that in most cases, scientists make decisions based on evidence gained from an experiment with extensive controls. But the differences in cannabinoid composition, varies from batch to batch, thus making cannabis experiments too organic for scientific rigidity.

So I needed to find a healthy and inexpensive way to make a nutritional Cannabis food supplement. A daily dietary supplement that was all natural and healthy, and a capsule that could be taken in large quantities without harmful side effects. But there were no commercial products that would meet my needs.

Then I began experimenting with different ingredients and different heating methods. This process took about two years before I came up with a novel, non-obvious and useful method to process the Cannabis plant into a food supplement.

And this novel, non-obvious and useful method is a process based upon the different pressings of the raw and cooked cannabis plant, combined with various fats, to produce different amalgams that holistically synergize to create the wholesome food product, and nutritional dietary supplement, called the Bioavailable Cannabis Plant Blend.

You see, I started researching more about the endocannabinoid system, and found out that all of the animals on this planet also have an endocannabinoid system. Then I had another 'crystallization moment', where I realized that the cannabis plant must be decarboxylated by using my discovered methods, so our livestock could also realize the efficacy of the cannabis plant.

I then delved into animal suffering, animal feed, and animal antibiotics; and realized that the cannabis feed, if processed correctly, could reduce animal suffering, could reduce the need for animal antibiotics, and could reduce the need to cultivate so much arable farmland, to feed our livestock with.

Following that realization, I started focusing on how to use the Cannabis Plant for addiction recovery. And I began to read about how the Cannabis Plant can help people with Heroin Addiction.

So I then extrapolated that understanding with the idea that the Cannabis Plant could help people relieve their Tobacco addiction, and their Nicotine Chemical addiction, as well. So I then came up with a blended recipe that could stand as a substitute for Tobacco Cigarette and Cigar Smoking, while at the same time, weaning the user off-of their Nicotine addiction.

Flowing that realization, I started researching various chemical compounds that would help create a smooth and impactful Smokeless Tobacco Replacement. And here is where I found out that the average Smokeless Tobacco is filled with some really nasty chemicals and fillers:

Chemicals like:

---

Arsenic: a poison used in insecticides, rat poison, and anchoring cement used to build houses
Cyanide: a poison found in chemical weapons and car exhaust
Polonium 210: a highly radioactive and chemically toxic element found in nuclear waste
N-Nitrosamines: cancer causing toxins found in brake fluid and granite counter-top cleaners
Formaldehyde: a cancer causing chemical found in glue and gas stoves. Also used to preserve corpses
Cadmium: found in motor oil and gear oil
Benzene: found in unleaded gasoline, car engine degreasers, insecticides, motor oil and paint
Lead: a poison found in high-mileage motor oil and ceramic glaze
Uranium 235: a toxic chemical used in nuclear reactors and nuclear weapons.

---

Then I started to realize, that for this nasty process to cease, we had to come up with a way for people to satisfy their cravings for the effects and rituals acquired during their Smokeless Tobacco addiction. Meaning, we still had to provide the ritual of smokeless tobacco, and we had to add various ingredients to enhance, smooth-out, and magnify the smokeless product experience, while also remembering to pre-decarboxylate the various cannabinoids found in the processed Cannabis Plant (while also remembering to add the raw cannabinoids, terpenes, and flavonoids).

SUMMARY

The 'Bioavailable Cannabis Plant' blending process is a novel, non-obvious and useful method to transform the Cannabis Plant into bioavailable and infused plant matter.

A primary object of the present invention is to provide an inexpensive method to commercially process the Cannabis plant into an impactful experience, so that the process overcomes the shortcomings of the other methods.

Another object is to provide a blending process to reduce the amount of wasted Cannabis Plant material that is being thrown away after current processing methods.

An additional object is to provide a cannabis product that can be stored for extended periods of time, and to process the cannabis plant into various blends.

Another object is to provide affordable cannabis plant products that can be used regularly.

*Further objects of the invention will appear as the description proceeds . . . .

Briefly described, in its preferred form, the present invention provides a method for preparing a commercially inexpensive way to produce high quality Cannabis Plant Blends. The present process preferably comprises the following steps:

high-heat-cooking (200° F.-350° F.) the raw cannabis plant for decarboxylation purposes;
and for a duration range of 1 minute to 3.5 hours;
saving a portion of the heat cooked and raw cannabis plant to be added back;
infusing various chemical compounds during the second high-heat cooking step;
and for a duration range of 1 minutes to 3.5 hours;
pressing and removing the first infusion of chemical compounds, to be added back;
infusing chemical compounds during the third heat cooking step (med 100° F.-200° F.);
and for a duration range of 7 hours to 13 hours;
pressing and removing the second infusion of chemical compounds, to be added back;
infusing various chemical compounds during the fourth heat cooking step (med. heat);
and for a duration range of 1 hour to 7 hours;
adding back a portion of the heat cooked cannabis plant during this third infusion step;
then after the forth heat cooking and third infusion step, add back removed pressings;
then add a portion of the raw cannabis plant, to create the final amalgam.

A fresh cannabis plant product at ambient temperature is the preferred initial product for the present process. That is, the most desirable final Cannabis product begins with a raw product in the beginning of the process. While an initially raw/fresh initial product is preferred, the present process can accommodate an initial cannabis product that has been frozen and-or cured, that is above or below ambient temperature, and that has already been dehumidified.

The heat-cooking temperature, and the time period the product stays within the cooking chamber, can be adjusted for the various decarboxylation processes, that the present invention is designed to handle. Each component step of the present invention can similarly be adjusted. Some of the adjustments can be incorporated by simply manipulating heat duration, and heat temperatures.

The preferable heat-cooking steps may comprise only one heat cooking step, multiple heat-cooking steps, and/or infusion heat-cooking steps with added chemicals compounds. Yet, if the product is not cooked with multiple heat cooking and infusion steps, then the final product lacks the amount of decarboxylated cannabinoids of the multiple heat cooked and infused amalgam.

In the conventional processing methods, they use extraction methods that contaminate the plant matter, or they simply extract certain cannabinoids and throw away what they don't need. One of the problems with this conventional process is that by using only concentrated and or isolated cannabinoids, the consumer won't realize the entourage effect, which is about the decarboxylated and raw cannabinoids synergizing for full efficacy.

In the present process, the various chemical compounds are added after convection cooking for the first time, and a raw portion of the cannabis plant is never heated so as to preserve the naturally occurring enzymes, vitamins, minerals, terpenes, terpenoids, and flavonoids. Thus, the product retains its full compliment of healthy ingredients because differently processed plant materials are added throughout the various blending steps; to create both the enhanced, and superior product, known as the 'Bioavailable Cannabis Plant Blend'.

If the cannabis plant is too hot at any point in the process, then many of the cannabinoids will be lost. If the cannabis plant is too cool during the heat-cooking process, then the cannabinoids won't decarboxylate and the product won't be made bioavailable.

Unlike the conventional processes, the present invention combines raw, heat cooked and infused aspects of the cannabis plant. Thus upon use, the biochemical affects can help upregulate the endocannabinoid immune system, which then helps provide a biochemical homeostasis, which can then help us self-heal through a daily healthful regimen.

This novel and useful 'Bioavailable Cannabis Plant' blending process, utilizes several steps in the production of the final product. Accordingly, an object of the invention is to provide a commercial process for preparing an affordable cannabis plant product that can be used regularly.

Now, please understand that the following terms all describe how to make the cannabis plant bioavailable: drying and curing, extracting, isolating, fractionating, concentrating, and heat-cooking; for all of these terms can involve the process called 'decarboxylation'. And it is imperative to note that many of these various processing methods consider the leftover plant-matter a 'contaminated waste product'.

In addition, it is imperative to understand that Dr. Sanjay Gupta hosted three CNN documentaries (Weed 1-3), where he taught about the 'entourage effect'. For you see, there are over 500+ chemical compounds found in the cannabis plant, and 100+ of those 500+ chemical compounds are known as cannabinoids. And when all of those cannabinoids are made bioavailable, the synergy of their combination actually creates what is known as the 'entourage effect'.

For example: 'THC' and 'CBD' are two of the 100+ cannabinoids found in the cannabis plant. And these cannabinoids start out with a carbon atom attached to the raw cannabinoid. This means that the raw cannabinoids are actually named 'THCA' and 'CBDA'. Therefore, the raw cannabinoids can only be made bioavailable after the decarboxylation of the various cannabinoids.

The drying and heating process is called the decarboxylation process and is different for each cannabinoid. Meaning, the duration of heat-time under certain temperatures determines when the cannabinoid has been decarboxylated, and therefore when the cannabinoid is made bioavailable. And the lower the temperature one uses, the longer it takes for decarboxylation; and the higher the temperature one uses, the shorter it takes for decarboxylation. The 'THC Decarboxylation Chart' was created in 1990 and found on the internet.

BRIEF DESCRIPTION OF THE DRAWING

FIG. 1: The prior art graph illustrates how heating time and temperature decarboxylated THCA, and affected the maximum bioavailability for the single cannabinoid called THC.

However, higher temperatures, and longer heat times, can also burn-off the various cannabinoids, vitamins, nutrients, minerals, enzymes, terpenes, and flavonoids found in the cannabis plant. I therefore had to come up with a novel, non-obvious and useful method to process the different pressings of the raw, cooked, and infused cannabis plant, to produce different amalgams that holistically synergize to create the entourage effect.

Meaning, I use multiple heat-cooking and infusion steps, press the plant matter to remove various infused amalgams, so I can then add the various infused amalgams back into the multiple heat cooked cannabis plant matter, so as to create the final blend. And by processing the cannabis plant in this way, I create no waste product, and I attempt to provide a full spectrum cannabis plant blend.

Again, it is very difficult to explain this process, and why it's so unique and novel. Bottom line, I use a non-obvious process to make the cannabis plant bioavailable, and I do so, by using different heat-cook temperatures, different heat-cook durations, and I do so by pressing and removing different infused amalgams that are then reincorporated back into the final cannabis plant blend.

DETAILED DESCRIPTION

The present invention provides a step-by-step process for transforming the raw cannabis plant into an infused and bioavailable cannabis-plant-blend. This step-by-step process produces a cannabis product, which is inclusive of an infused amalgam of either: both heat-cooked and raw cannabis, or just heat-cooked cannabis; along with an infused blend of various chemical compounds.

The twice, thrice, or four times heat cooked cannabis plant, with time-periods of resting and cooling, along with the optional steps of refrigeration and-or freezing, produces various bioavailable cannabinoids via multiple decarboxylation and cooling steps; and this unique and novel process utilizes a twice, thrice, or four-times heat-cooked cannabis amalgam that utilizes the cannabis plant; which is also blended and infused with various chemical compounds; so as to produce the final amalgam, which includes the utilized cannabis plant-matter, and has been named the bioavailable cannabis-plant-blend.

This step-by-step infusion and blending process entails the combining of both raw and decarboxylated cannabinoids, or just decarboxylated cannabinoids, via the utilization of the cannabis plant; along with the naturally occurring chemicals, enzymes, vitamins, nutrients, minerals, terpenes, and flavonoids that are found in the cannabis plant; along with the infused chemical compounds; for the purpose of creating an amalgam, which results in a blended cannabis product that has been designed to be ingested orally, sublingually, bucally, rectally, and by insufflation; or even utilized via inhalation.

The invention claimed is:

1. A process for transforming raw cannabis into a frozen four times heated and raw cannabis blend consisting essentially of:
   a) dehumidifying raw cannabis to yield dehumidified cannabis;
   b) heating the dehumidified cannabis at a temperature of between 200° F. and 350° F., for a time period between 1 minute to 3 hours, so as to produce a first heated cannabis;
   c) further heating the first heated cannabis at a temperature of between 200° F. and 350° F., for a time period between 1 minute to 3 hours, so as to produce a twice heated cannabis;
   d) pressing and fractioning out a first fraction from the twice heated cannabis;
   e) freezing both the first fraction and twice heated cannabis separately;
   f) further heating the twice heated cannabis at a temperature of between 100° F. and 199° F., for a time period between 3 hours to 13 hours so as to produce a thrice heated cannabis;
   g) pressing and fractioning out a second fraction from the thrice heated cannabis;
   h) freezing both the second fraction and thrice heated cannabis separately;
   i) further heating the thrice heated cannabis at a temperature of between 100° F. and 199° F., for a time period between 3 hours to 13 hours so as to produce a four times heated cannabis;
   j) adding-back the first and second fraction to the four-times heated cannabis;
   k) adding in more raw cannabis to the four times heated cannabis to produce a four times heated cannabis blend; and
   l) freezing the four times heated cannabis blend to produce a frozen four times heated and raw cannabis blend.

\* \* \* \* \*